United States Patent
Wirsen et al.

(10) Patent No.: US 8,563,612 B2
(45) Date of Patent: Oct. 22, 2013

(54) ANTIMICROBIAL AGENT COMPRISING A CYSTEINE COMPONENT COVALENTLY BOUND TO A SUBSTRATE IN PARTICULAR BY BINDING THROUGH AN S-S BRIDGE VIA A SPACER MOLECULE

(75) Inventors: Anders Wirsen, Vallentuna (SE);
Birgitta Agerberth, Stockholm (SE);
Gudmundur Gudmundsson, Reykjavik (IS); Jacob Odeberg, Stockholm (SE);
Torbjorn Lindberg, Stockholm (SE)

(73) Assignee: Cytacoat AB (SE)

( * ) Notice: Subject to any disclaimer, the term of this patent is extended or adjusted under 35 U.S.C. 154(b) by 41 days.

(21) Appl. No.: 11/886,759

(22) PCT Filed: Mar. 21, 2006

(86) PCT No.: PCT/SE2006/000350
§ 371 (c)(1),
(2), (4) Date: Jan. 17, 2008

(87) PCT Pub. No.: WO2006/101438
PCT Pub. Date: Sep. 28, 2006

(65) Prior Publication Data
US 2008/0153911 A1    Jun. 26, 2008

(30) Foreign Application Priority Data

Mar. 21, 2005   (SE) ........................ 0500629
Apr. 1, 2005    (SE) ........................ 0500729

(51) Int. Cl.
*A01N 37/12*    (2006.01)
*A01N 37/44*    (2006.01)
*A61K 31/195*   (2006.01)

(52) U.S. Cl.
USPC .......................................... 514/562

(58) Field of Classification Search
None
See application file for complete search history.

(56) References Cited

U.S. PATENT DOCUMENTS

| | | | |
|---|---|---|---|
| 5,543,391 A * | 8/1996 | Yatvin et al. | 514/2 |
| 5,932,183 A | 8/1999 | Batts et al. | |
| 6,159,495 A | 12/2000 | Timmons et al. | |
| 6,258,774 B1 * | 7/2001 | Stein et al. | 514/2 |
| 6,307,016 B1 | 10/2001 | Lehrer et al. | |
| 6,475,434 B1 | 11/2002 | Darouiche | |
| 6,838,435 B1 | 1/2005 | Krijgsveld et al. | |
| 7,078,380 B2 | 7/2006 | Cooper et al. | |
| 8,039,600 B2 | 10/2011 | Sedrani et al. | |

FOREIGN PATENT DOCUMENTS

| | | |
|---|---|---|
| CA | 2068894 A1 | 5/1991 |
| DE | 19935230 A1 | 2/2001 |
| JP | 54-007860 A | 1/1979 |
| JP | 05-503085 A | 5/1993 |
| JP | 05-336941 A | 12/1993 |
| JP | 08-259405 A | 10/1996 |
| JP | 11-509842 A | 8/1999 |
| JP | 2001-517422 A | 10/2001 |
| JP | 2004-513132 A | 4/2004 |
| RU | 2152984 C2 | 7/2000 |
| RU | 2175672 C2 | 11/2001 |
| WO | WO-93/17746 A1 | 9/1993 |
| WO | WO-94/24890 A1 | 11/1994 |
| WO | WO-9702287 A1 | 1/1997 |
| WO | WO-97/31093 A1 | 8/1997 |
| WO | WO-9915548 A2 | 4/1999 |
| WO | WO-00/33895 A1 | 6/2000 |

OTHER PUBLICATIONS

Huang et al. A Polyethylene Glycol Copolymer for Carrying and Releasing Multiple Copies of Cysteine-Containing Peptides. Bioconjugate Chemistry, 1998. vol. 9, pp. 612-617.*
Ali et al. Peptide delivery systems. Letters in Peptide Science. 2002. vol. 8, pp. 289-294.*
"International Application No. PCT/SE2006/000350 International Search Report", (Jun. 30, 2006),7 pgs.
Perez-Giraldo, C., et al., "Influence of N-acetylcysteine on the formation of biofilm by *Staphylococcus epidermidis*", *J Antimicrob Chemo*, 39, (1997),643-646.
Sheikh, C., et al., "Evaluation of in vitro antimicrobial and in vivo cytotoxic properties of some novel titanium-based coordination complexes.", *Biol Pharm. Bull.*, 27(5), (May 2004),710-3.
"International Application Serial No. PCT/SE2006/000350, Written Opinion mailed Jun. 30, 2006", 10 pgs.
Ljungquist, C., et al., "Thiol-directed immobilization of recombinant IgG-binding receptors", *Eur. J. Biochem.*, 186(3), (1989), 557-561.

(Continued)

*Primary Examiner* — Marcela M Cordero Garcia
(74) *Attorney, Agent, or Firm* — Schwegman Lundberg & Woessner, P.A.

(57) ABSTRACT

The invention relates to an antimicrobial agent where a cysteine compound is covalently bound to a substrate, in particular by binding through an S—S bridge via a spacer molecule to the substrate. The spacer comprises a carbon chain, optionally interrupted by one or more heteroatoms, e.g. O, S, N, P and Si; the chain is optionally substituted with one or more alkyl groups, preferably lower alkyl groups with 1-5 carbon atoms, hydroxyl groups or alkoxy groups. Also, the invention refers to a substrate that is coated with the antimicrobial agent of the invention. The agent has excellent antimicrobial properties and can be used to coat surfaces and substrates of various devices, such as medical devices or devices used in food handling, in order to prevent or inhibit accumulation and/or growth and/or proliferation and/or the viability of microorganisms and/or formation of biofilm.

17 Claims, No Drawings

(56) References Cited

OTHER PUBLICATIONS

Oosterhof, J., et al., "The influence of Antimicrobial Peptides and Mucolytics on the Integrity of Biofilms Consisting of Bacteria and Yeasts as Affecting Voice Prosthetic Air Flow Resistances", *Biofouling*, 19(6), (2003), 347-353.

Parry, M. F., et al., "Effect of N-Acetylcysteine on Antibiotic Activity and Bacterial Grown In Vitro", *Journal of Clinical Microbiology*, 5(1), (1977), 58-61.

Schwandt, L. Q., et al., "Prevention of biofilm formation by dairy products and N-acetylcysteine on voice prostheses in an artificial throat", *Acta Otolaryngol*, 124(6), (2004), 726-731.

"Canadian Application Serial No. 2,601,459, Office Action mailed May 31, 2012", 6 pgs.

"Chinese Application Serial No. 200680007563.7, First Office Action mailed Mar. 16, 2010", (English Translation), 6 pgs.

"Chinese Application Serial No. 200680007563.7, Second Office Action mailed Jan. 4, 2012", 7 pgs.

"Chinese Application Serial No. 200680007563.7, Third Office Action mailed Aug. 28, 2012", 5 pgs.

"European Application Serial No. 06717035.7, Office Action mailed Mar. 19, 2012", 1 pg.

"European Application Serial No. 06717035.7, Response filed Sep. 10, 2012 to Office Action mailed Mar. 19, 2012", 16 pgs.

"International Application No. PCT/SE2006/000350 International Preliminary Report on Patentability dated Sep. 25, 2007", 11 pgs.

"Russian Application Serial No. 2007135048, Official Action", (English Translation), (2012), 5 pgs.

"European Application Serial No. 06717035.7, Supplementary European Search Report mailed Feb. 29, 2012", 11 pgs.

"Japanese Application Serial No. 2008-502947, Office Action mailed Nov. 8, 2011", (English Translation), 4 pgs.

Disbudak, A., et al., "Cysteine-metal affinity chromatography: determination of heavy metal adsorption properties", *Separation and Purification Technology*, 26(2-3), (2002), 273-281.

Duan, X., et al., "Improved haemocompatibility of cysteine-modified polymers via endogenous nitric oxide", *Biomaterials*, 23(41, (2002), 1197-1203.

Jurbergs, H. A., et al., "Characterization of Immobilized Poly(:L-cysterine) for Cadmuum Chelation and Preconcentration", *Analytical Chemistry*, 69(10), (1997), 1893-1898.

Olofsson, A.-C., et al., "N-Acetyl-L-Cysteine Affects Growth, Extracellular Polysaccharide Production, and Bacterial Biofilm Formation on Solid Surfaces", *Applied and Enviornmental Microbiology*, 69(8), (2003), 4814-4822.

"Australian Application Serial No. 2006225382, Examination Report mailed Feb. 7, 2013", 3 pgs.

"Canadian Application Serial No. 2.601,459, Office Action mailed Jan. 21, 2013", 3 pgs.

"Chinese Application Serial No. 2006800075637, Notice of Allowance mailed Dec. 25, 2012", (w/English Translation), 8 pgs.

"Indian Application Serial No. 6925/DELNP/2007, First Examination Report dated Feb. 27, 2013", 2 pgs.

"Japanese Application Serial No. 2008-502947, Japanese Decision to Grant a Patent dated Feb. 12, 2013", 3 pgs.

"Korean Application Serial No. 10-2007-7021959, Office Action dated Feb. 12, 2013", (w/ English Translation), 12 pgs.

\* cited by examiner

ANTIMICROBIAL AGENT COMPRISING A CYSTEINE COMPONENT COVALENTLY BOUND TO A SUBSTRATE IN PARTICULAR BY BINDING THROUGH AN S-S BRIDGE VIA A SPACER MOLECULE

RELATED APPLICATIONS

This application is a nationalization under 35 U.S.C. 371 of PCT/SE2006/000350, filed Mar. 21, 2006 and published as WO 2006/101438 A1 on Sep. 28, 2006, which claimed priority under 35 U.S.C. 119 to Sweden Patent Application Serial No. 0500629-1, filed Mar. 21, 2005 and Sweden Patent Application Serial No. 0500729-9, filed Apr. 1, 2005; which applications and publication are incorporated herein by reference and made a part hereof.

TECHNICAL FIELD

The invention refers to antimicrobial agents or devices that come in contact with microorganisms and/or that is desirable to keep free from accumulation and/or adhesion of microorganisms. The substrate or device surface exhibits an antimicrobial agent of the invention.

TECHNICAL BACKGROUND

In various situations and applications of e.g. medical care, food handling and food storing it is very important that devices and products that are used are kept free from growth or proliferation of microorganisms. Not the least is this extremely important when it comes to medical devices that are brought into contact with patients in a hospital, since contaminated devices may participate in spreading of disease and microorganisms in a way that may severely affect the health of many patients.

It would for instance be very advantageous if the devices and products that come into contact with potentially harmful microorganisms had the capacity to inhibit or kill bacteria and/or other microorganisms, such as virus and fungi, in order to prevent the spreading of diseases.

The objective is to prevent the initial colonization that subsequently may develop into a biofilm. The initial phase of colonization may be suppressed by either inhibition or the killing of micro-organisms.

In order to obtain such a protection it is known to provide a surface in a device with metal ions, such as ions of the elements Ag and Ni. Often Ag is applied as an alloy with the purpose to release the Ag$^+$-ions at a suitable rate to the environment, thereby preventing the accumulation of microorganisms.

However, one problem with this solution is the adhesion of the metal or alloy to the surface in question. Also, the antimicrobial effect is not easily controlled, and Her the metal ion coated surface may have cytotoxic effects.

U.S. Pat. No. 6,475,434 discloses a biofilm penetrating composition for removal of biofilms formed and constituted by infectious microorganisms as well as for coating medical devices in order to prevent formation of such biofilms. The composition comprises cysteine and analogues or derivatives thereof to be selected as one of the components. The role of the cysteine or cysteine related component is unclear and notably for coating applications they are used in combination with known antimicrobial agents such as rifamycines, tetracyclines and penicillines. Notably, as shown in examples 2 and 3 in U.S. Pat. No. 6,475,434, the only cysteine component tested (which is N-Acetyl Cysteine) has no effect unless combined with the antibiotics tested. Furthermore for biofilm protection all components are applied by impregnation of the device or mixing with the device material during manufacturing. The components then become physically bound by adhesion and penetration into the device material, which means that their function to a large extent occurs upon their release to the environment. Particularly in medical application such concepts require strict control of the balance between antimicrobial, cytotoxic and immunogenic effects. Since diffusion is time and temperature dependent, storage and durability of the coated devices also become matters of serious concern.

It has been described by Olofsson et al. (Applied and Environmental Microbiology, August 2003; 69(8), 4814-4822) that N-Acetyl Cysteine can affect bacterial growth in solution. Other effects of N-Acetyl Cysteine were to diminish the adhesion of multi-species bacteria onto stainless steel surfaces or facilitating the detachment of a biofilm on stainless steel surfaces.

A primary purpose of the present invention is to provide an antimicrobial agent having the capability to prevent or at least substantially reduce the accumulation and/or adhesion of individual microorganisms on the surface of a device in a sable and long-term manner.

This purpose is fulfiled by the inventors in a first aspect of the invention, referring to an antimicrobial agent cowing a subs with a covalently bound cysteine compound.

In particular, the invention provides an antimicrobial agent wherein the cysteine compound is bound through an S—S bridge via a spacer molecule to the substrate. The spacer comprises a carbon chain, optionally interrupted by one or more heteroatoms, e.g. O, S, N, P or Si, and the chain is optionally substituted with one or more alkyl groups, preferably lower alkyl groups with 1-6 carbon atoms, hydroxyl groups or alkoxy groups. In the examples given below the cysteine compound is bound in a terminal position of the spacer via an S—S bridge, which is a preferred embodiment of the invention. However, also other positions in the spacer chain are possible as long as the cysteine function is exposed to the environment.

According to a preferred embodiment of the invention the cysteine-containing ligand bound to a substrate has the general formula:

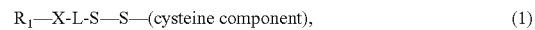

$$R_1\text{—X-L-S—S—(cysteine component)}, \qquad (1)$$

wherein $R_1$ is a soluble or insoluble substrate; e.g. a solid surface or a soluble organic molecule or polymer.

X is a linking group from the coupling reaction between the substrate and L.

L is a spacer molecule selected from the group comprising $(CH2)_m$ where m is 1-20, preferably 1-12, 1-8 or 1-6; $(CH_2CH_2O)_n(CH_2)_p$ or $(CH(CH_3)CH_2O)_n(CH_2)_p$ where n is 1-1000, preferably 1-100 or 3-50, and p is 1-20, preferably 1-12, 1-10 or 1-6. The $(CH2)_p$ segment is bound to the disulphide bridge but may optionally also occur between the $(CH_2CH_2O)_n$ and/or $(CH(CH_3)CH_2O)_n$ segments in a block co-polymer;

Cysteine component is herein referred to as the residue of a cysteine compound comprising cysteine, a cysteine analogue or cysteine derivative providing antimicrobial act which is substantially the same or on a comparable level to that confer by cysteine It has been noticed that an embodiment of the invention where the cysteine compound is bound via an S—S bridge comprising one S from the thiol group of cysteine compound and one S from the spacer molecule is of special importance, at least in some applications, due to its superior antimicrobial activity.

Accordingly, an antimicrobial agent is provided that is covalently attached to the of the device, and which, due to the surprisingly advantageous effects of covalently bound cysteine, has a high and long-term effect; see the examples below, on individual microorganisms, thereby preventing or substantially inhibiting the adhesion and accumulation of individual microorganisms. Thus, the present invention offers a huge potential for all applications wherein it is desirable that a surface or substrate will exhibit antimicrobial/antibacterial properties. A flier and essential advantage of the invention, is that it has been shown by the inventors that the agent of the invention appears to lack cytotoxic effects, which makes it usable in many different applications.

In one aspect of the present invention various devices that are desirable to keep free from accumulation and/or adhesion of microorganisms are coated completely or partially with an antimicrobial agent according to the invention.

In a further aspect, the present invention refers to the use of an antimicrobial agent of the invention for preventing growth and/or proliferation of microorganisms on a substrate and/or a surface of a device.

In contrast to U.S. Pat. No. 6,475,434, the present invention provides a method to have the cysteine or cysteine related component covalently bound to a substrate. A major use for the invention is to provide an antimicrobial coating to a solid device. By this concept the antimicrobial agents are permanently attached to the surface and the antimicrobial effect occurs upon surface contact rather than from reaction with released agents which will largely decrease the risk of adverse effects in a biological environment. This is a major difference compared to the prior art methods where cysteine is provided as such a release agent. Also by covalent attachment the surface can be made more specified in terms of surface concentration and chemical structure. Thus not only the surface bound cysteine or cysteine related component itself but at least in some applications also the disulphide bond by which it is linked to the surface is one of the inventive features of the present concept with regard to antimicrobial effect. Furthermore, the covalent attachment provides a surface, which in situ as well as in storage is superior in consistency and durability compared to surfaces where diffusion and leakage of the active agents are of major concern.

"An antimicrobial agent" comprises a substrate which has been modified to exhibit a covalently bound cysteine component and has the effect of preventing, or at least substantially preventing accumulation, growth and/or proliferation of at least one specific microorganism. This effect can e.g. be observed by methods known in the art, e.g. by the methods used in the example section of this disclosure.

A "cysteine component" comprises the residue of cysteine, a cysteine analogue or cysteine derivative having antimicrobial effect, e.g. homocysteine or N-substituted cysteines such as N-acetyl-L-cysteine and N-alkylated cysteines.

"Substrate" ($R_1$) comprises any article, device, molecule or polymer, soluble or insoluble that can be functionalized to obtain antimicrobial properties by binding a cysteine component. Of special interest are solid articles like medical devices to be used inside or in contact with the human or animal body, in particular sensitive tissues and body fluids. This list of potential applications is extensive, see further below, and includes implants, tubings drainage catheters, etc to be used in e.g. extracorporeal applications, drainage (e.g. ear or hydrocephalus), dialysis, contact lenses, intraocular lenses, artificial skins, dialysis equipments, heart and lung machines, suture materials, wound care devices, dental products, parenteral administration, drug delivery, stents, pumps (e.g. for insulin), hearing aid devices, syringes, suture materials, pacemakers, etc.

"Preventing" or "inhibiting" comprises the capacity to stop or substantially reduce growth and/or proliferation and/or accumulation and/or substantially reduce viability of microorganisms at a position where the agent of the invention is present The main potential of the present invention is to offer the possibility to provide an antimicrobial surface on a solid device, which potentially comes in contact with microorganisms, and which is desirable to keep free from accumulation and/or proliferation of microorganisms and/or serve as a reservoir for viable microorganisms. The great number of devices to be used in medical as well as food-handling applications where the presence of microorganisms can be more or less dangerous, illustrates the potential of this invention. In order to make this possible, the inventors have successfully used the substance cysteine, which the inventors have shown to have unexpectedly strong antimicrobial effect when covalently bound as described and claimed here. Antimicrobial effects have been shown for cysteine analogues and derivatives as well, like N-acetylcysteine and homocysteine.

Polymers or oligomers of ethylene oxide and propylene oxide i.e. poly(ethylene oxide) or poly(ethylene glycol) are readily water soluble and furthermore poly(ethylene oxide) have protein repelling properties, which may be added to the antibacterial function of this invention especially when used in connection with surfaces. Depending on the cysteine component, the following structures are examples of suitable ligands to be used:

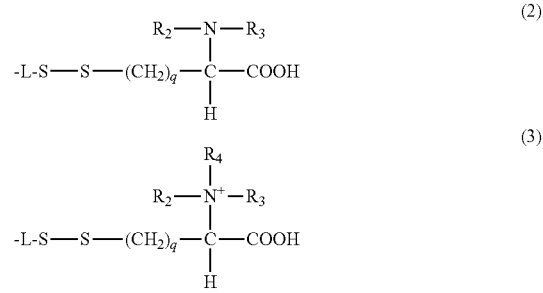

In formula (2) the substituents $R_2$, $R_3$ may be hydrogen or alkyl with 1 to 20, preferably from 1 to 12, more preferably 1 to 6 carbon atoms in any combination of $R_2$ and $R_3$ and q may have the same variation as m and p for the methylene constituents of the L segment as previously described i.e. from 1 to 20, preferably from 1 to 12, more preferably from 1 to 6. When q=1 and $R_2$=$R_3$=H the cysteine component becomes a cysteine residue which like the cysteine homologues and derivatives is coupled via its thiol group which contributes with one sulphur to the disulphide bond. In addition to direct alkylation of the cysteine amino group $R_2$ and $R_3$ alkyls may be bound via an amide bond comprising the nitrogen of the cysteine component, e.g. when $R_2$ is hydrogen and $R_3$ is methyl, the cysteine component becomes acetylcysteine.

In formula (3) $R_2$, $R_3$, $R_4$ are alkyl substituents which give a positively charged quartenary amino group. In this case the number of carbon atoms in the alkyl chains of the $R_2$, $R_3$, $R_4$ substituents may vary between 1 and 25, preferably from 1 to 18 in any combination. Further, q may have the same variation as m and p for the methylene constituents of the L segment as previously described i.e. from 1 to 20, preferably from 1 to 12, more preferably from 1 to 6.

Depending on pH, charged ionic groups may also occur as protonized amino groups in (2) and carboxylate-groups in (2) and (3).

The coupling —X— between the subs $R_1$ and the ligand is obtained by chemical reactions between functional groups on $R_1$ and the respective ligand. If $R_1$ has a chemical functionality Y and a ligand functionality Z which upon reaction gives X, the principal coupling reaction where by-products are omitted may be written as:

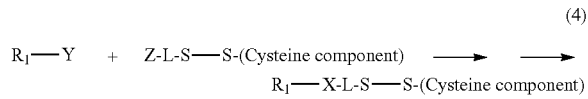

(4)

$R_1$—Y + Z-L-S—S-(Cysteine component) ⟶ ⟶
$R_1$—X-L-S—S-(Cysteine component)

Depending on the choice of Y and Z and the reaction conditions the X group obtained may be amide, secondary amine, ester, ether, hydrazine, urethane, urea, carbonate and others. A large number of specific and efficient reactions are available which are well established in organic chemistry. The Y, Z and X groups as well as the reactions given here are therefore examples and not limiting for the invention.

TABLE 1

| | | | |
|---|---|---|---|
| (a) | when Y = COOH | and Z = $NH_2$ | then X = CONH |
| (b) | when Y = COCl | and Z = $NH_2$ | then X = CONH |
| (c) | when Y = COOH | and Z = OH | then X = COO |
| (d) | when Y = COCl | and Z = OH | then X = COO |
| (e) | when Y = $NH_2$ | and Z = CHO | then X = NH |
| (f) | when Y = $NHNH_2$ | and Z = CHO | then X = NHNH |
| (g) | when Y = $NH_2$ | and Z = NCO | then X = NHCONH |
| (h) | when Y = $NH_2$ | and Z = OCOOϕ$NO_2$ | then X = NHCOO |
| (i) | when Y = $NH_2$ | and Z = Succinimidyl- | then X = NHCO |
| (j) | when Y = $NH_2$ | and Z = Epoxy- | then X = $NHCH_2CH(OH)$ |
| (k) | when Y = OH | and Z = NCO | then X = OCONH |
| (l) | when Y = OH | and Z = Epoxy | then X = $OCH_2CH(OH)$ |
| (m) | when Y = $OSO_2CH_2CF_3$ | and Z = $NH_2$ | then X = $CH_2NH$ |
| (n) | when Y = $OSO_2CH_2CF_3$ | and Z = SH | then X = $CH_2S$ |
| (o) | when Y = SS | and Z = SH | then X = SS |
| (p) | when Y = $(alkyl)_3COK$ | and Z = (alkyl)Br | then X = O |
| (q) | when $R_1$ = Au, Ag | and Z = SH | then X = S |
| (r) | when $R_1$ = Au, Ag | and Z = SS | then X = S |
| (s) | when $R_1$ = $R_1$• | and Z = $CH_2$=C— | then X = CH—C— |

The Y and Z groups in examples (a) to (p) may be interchanged between $R_1$ and the ligand to give the same X link although inverted between $R_1$ and the ligand. For example when the functional groups in (a) are interchanged to Y=$NH_2$ and Z=COOH the X link becomes HNOC. In examples (e) and (f) the initially obtained imine generally known as a Schiff base is reduced to the secondary amine link with $NaCNBH_3$. Often intermediate steps are used to increase selectivity and yield. Well known examples are activation of the carboxylic group (Y) in (a) with a carbodiimide and/or N-hydroxysuccinic imide prior to the amide formation with the amino group (Z). Amine groups may be activated with disuccinimidyl carbonate to form urea link with another amine group.

In addition to carboxylic and amino groups hydroxylic groups are also useful in a large number of coupling reactions:
after derivatisation into carbonates giving the Z group in
(h) where ϕ denotes a benzene ring or into tresylated groups as in (m) and (n)
after activation of hydroxylic groups by derivatisation into tosyl- or succinimidyl carbonate groups or treatment with $Br_2$ or CNBr for coupling reactions with nucleophiles like amines and/or thiols.
two hydroxylic groups may be linked together with phosgene to form a carbonate link.

Comprehensive reviews on coupling chemistry with the reactions mentioned here as well as additional coupling reactions are found in the lyre (Ref. Herman S. et al. J. Bioact. Compat. Pol. 1995, 10, 145-187)

In example (s) in Table 1, $R_1$. symbolizes a solid substrate with free radicals accessible for reaction with an unsaturated group exemplified but not limited to ethylenic, acrylic or metharylic double bonds. By using monomers which have the ligand -L-S—S-(cysteine component) attached to reactive carbon-carbon bonds, oligomeric or polymeric chains may be obtained which are covalently bound to the substrate and which have the ligand as side groups. The concentration of these side groups in the oligomeric or polymeric chains may be controlled by copolymerisation with suitable monomers exemplified by but not limited to acrylic or methacrylic acids or esters or acrylamide. Another route would be to use monomers like maleic acid, maleic anhydride, tiglic acid or allyl amine which readily bind to a free radical providing surface but have strongly reduced chain propagation. The functional groups given by these monomers, i.e. anhydride, carboxyl or amine will therefore become confined to a very thin surface layer on the substrate. By this route each coupling of ligand will occur essentially by terminal attachment directly to functional groups on the surface thus providing a different structure as compared to that obtained when the ligand takes part in graft polymerization.

The coupling reaction with $R_1$—Y may occur according to (4) provided that the Y group reacts selectively with the Z group of the ligand and not with amino or carboxylic groups in the cysteine component.

In cases were the Y group may not react exclusively with the Z group of the ligand represented by:

Z-L-S—S-(Cysteine component)　　(5)

but also with the amino and/or carboxylic group of the cysteine component these groups may, if required, be protested by substitution and esterification respectively. The amino group may be protected by substituents exemplified by tertiary butyloxycarbonyl (t-BuO). This is of course only necessary when the amino group is not alkylated into tertiary or quartenary amines as defined in equations (2) and (3). The carboxyl group of the cysteine component may be protected by methylation. After the coupling reaction between $R_1$—Y and the Z-ligand to obtain the X linked ligand as in equation (4) the t-BuO and the ester-methyl groups may be removed by acid and alkaline hydrolysis respectively and thus restoring the original structure of the Z ligand. With these options the Z-ligand as defined in equation (2)-(4) and by formula (5) and furthermore available with various Z functionalities is a separate item of this invention to be used as a kit component for single step modification of functionalised surfaces. This aspect of the invention also covers the example previously described where the functionality Y of the substrate is a free radical and the functionality Z of the ligand is an unsaturated reactive carbon-carbon bond.

When the functional group Y is bound to a solid substrate the ligand may be synthesized in situ on the substrate surface. This has the advantage that unreacted Y groups as well as by-products are eliminate in intermediary steps.

By this procedure the first step will be to react the $R_1$—Y surface with a compound having the general composition

where L have the same definition as before and where the substituent $R_5$ is easily replaced upon reaction with thiols to give a new disulphide bond with a thiol compound.

The first coupling step may be expressed as:

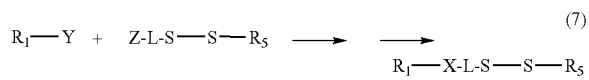

and the following step:

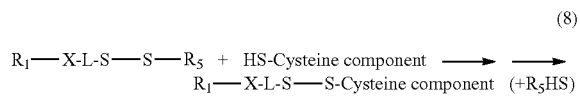

A common example of $R_5$ is pyridinyl but dansyl is also used. Alternatively the disulphide bond in (6) may belong to a thiosulphate group which will also give a disulphide linkage upon reaction with a thiol.

In addition there is an alternative route for obtaining essentially the same chemical structure as before and which is also within the scope of this invention. In this case a thiol segment or group -L-SH is bound to $R_1$ via the coupling group X and where L and X are defined as before and —SH is a terminal thiol group. This may react exclusively with the thiol group of the cysteine component in the presence of oxidants to form the disulphide link with the cysteine component:

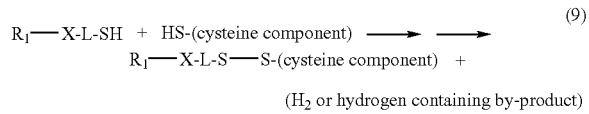

When finally the cysteine component is coupled according to formula (9) an antimicrobial ligand is obtained which is covalently bound to $R_1$, as schematically shown in formula (9).

Surface functionalization of polymeric materials such as plastics, rubber, cellulosics etc. may be achieved by grafting or adsorption of compounds carrying functional grows, such as for example carboxyl or amine. Grafting which gives a covalent link to the substrate requires functionalization of the surface. Compounds which can react with free radicals are grafted during or after activation with UV, electron beam or gamma irradiation or gas plasma. By these methods free radicals may be generated in polymeric substrates which may initiate graft polymerization onto such substrates. These methods of surface modifications for solid polymeric substrates are represented by example (q) in Table 1. In this process the grafting usually involves chain propagation from the substrate surface known as graft polymerization.

Monomers which are frequently used in free radical graft polymerization are acrylic compounds like acrylic acid, methacrylic acid and their esters or acryl amide as well as vinyl pyrrolidone. By graft polymerisation of such monomers containing functional groups e.g. carboxyl, amino, halogens etc, a solid surface may be provided with covalently bound functional groups for covalent attachment of the antimicrobial ligand. A special application of graft polymerisation also comprised by the present invention was previously described where the antimicrobial ligand as depicted in formula (6) could be graft polymerized when Z is a free radical reactive group containing reactive unsaturated carbon-carbon bonds. This would give antimicrobial ligands as side groups in the graft polymerized chains the concentration and location of which may be controlled by graft co-polymerization with suitable vinylic or acrylic monomers. However, as was also previously described, the antimicrobial ligand may be terminally attached directly to the substrate. In this case the functionalisation of the substrate is made in a first step by monomolecular grafting with unsaturated compounds having insignificant chain propagation like maleic anhydride, maleic acid and triflic acid or a self terminating monomer like allyl amine. By this procedure functional groups may be generated on the surface for direct terminal attachment of the antimicrobial ligand by chemical coupling. Also in cases when a vinylic or acrylic ligand in formula (6) will not polymerize e.g. for steric reasons it would attach directly by terminal reaction with free radicals on the substrate.

In cases where the substrate as such is a hydrolyzable plastic material like polyester (PET), polyamide (Nylon™, Nomex™, Kevlar™) or polyacrylate (PMMA) surface functionalization may be obtained by hydrolysis in a basic or acid solution. Polyesters would give carboxylic and hydroxylic groups and polyamides carboxylic and amine groups, which may be used in subsequent modifications by coupling or adsorption.

Metallic substrates like stainless steel may be surface functionalised with carboxylic groups by radiation and plasma treatment. Medical articles like stents are carboxylated by exposure to gas plasma of silane and acrylic acid. Gold and silver surfaces may be grafted by using their reactivity towards thiol and disulphide compounds, which would also carry other groups like carboxyl or amine. Also for metallic substrates free radical grafting of surfaces may be obtained by cathodic polarization of the conductive substrates during exposure to monomers capable of forming covalent links upon reaction with free radicals. The surface grafting is analogous to that for solid polymeric substrates in terms of initiation, propagation and monomers and is also represented by example (s) in the table on table 1.

When surface modification of polymeric substrates is made through adsorption the substrate priming is often made by chemical oxidation, corona treatment or oxidative gas plasma to obtain hydrophilic and ionic groups in the surface layer. One example is the adsorption of polyethylene imine onto polymeric substrates which have been oxidized with permanganate or persulphate. The amino surfaces obtained may be used for chemical coupling reactions as well as adsorption of negatively charged polymers like polyacrylic acid, dextrane sulphate or heparin at suitable pH. Often such polyelectrolytes in their ionically charged states are adsorbed in alternating layers with the properties of interest in the outmost layer. Especially carboxylation of metallic surfaces is often made by adsorption of polyacrylic or polymethacrylic acid. As described above they may then be aminized by chemical coupling or by ionic adsorption of for example polyethylene imine or polyallylamine. Another way to obtain adsorption, which does not need any primary functional on of the substrate, is to use block copolymers having both hydrophobic and hydrophilic blocks or segments which will selectively adsorb to and functionalize the substrate surface. Typical such block copolymers are polyethylene glycol-polypropylene (Pluronics) and polycrylates—polystyrene, polyacrylates—polyethylene, polybutadienes—polystyrene and others which may also contain amino or carboxylic functionalities.

By definition the antibacterial ligand -L-S—S-(cysteine component) of this invention is always covalently bound to a substrate, $R_1$.

However, since the definition of $R_1$ includes organic and polymeric compounds, $R_1$ will also cover polymers which subsequently are capable of binding to a solid substrate by covalent binding or adsorption.

The options for covalent binding of the antibacterial agent of this invention onto a solid substrate are emphasized by the definition of $R_1$, comprising that attachment of the antimicrobial agent to a solid substrate by adsorption. In this case $R_1$ is a soluble substrate, exemplified by e.g. ionizable polymers like polyethylene imine or polyacrylic acid or block copolymers with hydrophobic/hydrophilic blocks like polyethylene glycol-polypropylene glycol or polyacrylates in block copolymers with polystyrene, polyethylene and others. The cysteine component is covalently bound to a soluble substrate which in a further step is immobilized on a solid substrate as described here.

Thus, the surface modifications as well as the subsequent chemical coupling or adsorption used to attach the antibacterial agents may be performed by many different routes. In addition the substrates may be organic or inorganic materials comprising synthetic or natural polymers as well as metals and minerals. Therefore the methods, chemical reactions and substrates, which are presented here and in the examples below, are only descriptive and not limiting for obtaining the antibacterial agents and surfaces covered by the invention.

The surface concentration of the agent of the invention, such as L-cysteine, is in the interval from $10^{-11}$ from $10^{-4}$ mole/cm$^2$, and preferably in the interval from $10^{-9}$ to $10^{-5}$ mole/cm$^2$.

In order to obtain inhibition of clinically or technically important microorganisms a 100-folded inhibition is preferably achieved in accordance with the invention with respect to adherent viable bacteria that can be released with the assay, staring with a large exposure (titer of 400 000 cfu/ml in the staring culture). This may partly be dependent on the specific organism and the degree/titer of exposure. The tested conditions vastly exceed what can be expected in the actual clinical situation.

Examples of microorganisms, for which the invention may be used to prevent growth and/or proliferation of, are anaerobic and aeorbic bacteria that encompass both different Gram-positive bacteria chosen from, but not limited to, different species of *Staphylococci* such as *S. aureus, S. epidermides* and other coagulase-negative *staphylococci, S. saphrophyticus, Enterococcus* spp, *Nesseriae* (*Meningococci Gonococci*), *Streptococci* (Viridans, hemolytic and non-hemolytic, group B and D, *S. pneumoniae*), *Chlostridia* (*perfringens, botulinum*), *Bacillus megaterium*, as well as different Gram-negative species chosen from, but not limited to, different *Enterobacter* spp, *Escherichia coli, Kiebsiella* spp, *Proteus, Campylobacter, Yersinia, Shigella, Salmonella, Hemophilus* (*influenza*), *Barteriodes* (*fragilis, bivius*), *Pseudomonas* (*aeruginosa, cepacia*), *Legionella* (*pneumophilia*). Also included are different *mycoplasma* species and *candida* species and different fungi. Preferred examples of bacteria are the Gram-positive bacterium *Staphylococcus aureus*, the Gram-negative bacterium *Escherichia coli*, or the Gram-positive bacterium *Bacillus megaterium*.

The invention can be used to prevent or inhibit growth of microorganisms on surfaces of different applications that can cause a problem due to colonisation or infection. It has here been shown to be effective against both Gram positive and Gram negative bacteria (the Gram negative bacterium *Escherichia coli*, or the Gram positive bacterium *Staphylococcus aureus* and *Bacillus megaterium*). Several different microorganisms have been described in relation to catheter colonisation and infection in the health care sector and hospital environment. These microorganisms include, but are not limited to, Gram positive and Gram negative bacteria listed below. Also different fungi are a frequent problem, especially in immuno-compromised patients (undergoing transplantation, or otherwise immunosuppressive therapy etc). The invention can be utilised where infection, colonisation or biofilm formation on artificial devices (catheters, trachiostomi tubes etc) can be a problem in health care. Examples of microorganisms known or described to be catheter borne, and against which the invention can be used, are (but not limited to): *Staphylococci* spp (such as *S. aureus, S. epidermides* and other coagulase-negative *Staphylococci* like *S. saprophyticus*); *Streptococci* spp (viridans, hemolytic and non-hemolytic, group B and D, *S. pneumoniae; Enterococcus* spp, *S. facealis; Chlostidia* (*perfingens, botulinm*); Different *Enterobacter* spp, like *Escherichia coli, Klebsiella* spp (pneumonia), *Enterobacter cloace, aerogenes, Proteus*, (*mirabilis*), *Campylobacter, Yersinia, Shigella, Salmonella, Hemophilus* (*influenza*), *Neisseriae* (*meningococcus* and *gonococcus*), *Bacteroides* (*bacteroides* Spp. and *fasobacterium*), *Pseudomonas* (*aeruginosa, cepacia*), *Legioneila* (*pneumophilia*), *Sertatia marcenens, Acinetobacter* spp, *Morganella morganii, Stenotrophomonas, Citrobacter* spp, *Corynebacterium* spp, *Burkholder Cepafia, Acinetobacter* spp; Different *Mycoplasma* species (*M. avian* and other); and also fingi such as *Candida* spp, *C. tropicales, C. parapsilosis, Cryptococcus neoformans, Aspergillus fumigatus, Tricosporun, Blastoschizomyces, Stenotrophomonas maltophilia, Malassezia, Bukholderia cepafa, Aspergillus*.

In many applications of the present invention, the substrate is apart of a device, an apparatus and/or a surface chosen from (a) medical devices, such as extracorporeal medical devices, which are applicable at the exterior of the human or animal body or infracorporeal medical devices, which are applicable in the interior of the human or animal body, (b) grocery devices, and (c) other devices. The examples of applications listed below are only intended to demonstrate the potential of the invention without in any way being limiting.

Medical devices (a) comprise applications chosen from:
    artificial skin or cove for burning wounds
    dialysis (tubings from an to the dialysis device)
    ear drainage (drainage from a cavity, wound or abscess or
       within the interior of the ear)
    ear implants (implant within the interior of the ear)
    hearing aid device (interiorly placed hearing device)

heart and lung machine tubings (tubings from and to the heart and lung machine device)
hydrocephalus drainage (drainage from the brain region/ventricles)
syringe (disposable syringes)
stomis (stomi devices)
suture materials (suture devices)
wound care (wound care devices, such as plaster).
catheters (disposable and permanent catheter devices, e.g. central venous catheters (CVC), peripheral venous catheters (PVC), peripherally inserted central catheters, urinary catheters, and peritoneal catheters)
dental products (products implanted in the mouth region)
implants in the body (bones, pro paradontit (products implanted in the mouth region))
insulin pump (tubings from and to the insulin pump)
nerve guidelines (guiding devices for nerves)
pacemaker (pacemaker and its surrounding devices)
postoperative drainage (drainage devices subsequent to surgery)
drainage from regions and/or organs and cavities within the human body (abscess, nephrostomi and similar)
intracorporeal/intraluminal stents (stents used to keep different lumen open, for example in the vascular system and vessels, in organs and tissue, in the intestinal system, bile ducts etc)
tubing or equipment used for parenteral administration of liquids, solutions, infusions, drug delivery.

Grocery devices (b) comprise applications chosen from:
contact for fresh food or subsumes or devices used in food processing (surfaces that may be in contact with bacterial sources)
drug packages (to keep the opening free of bacterias) packaging for sensitive drugs)
milking devices (devices subjected to bacterial sources during milking operations)
sprinkler devices (sprinkler devices and other wax transporting devices that may be colonised by microorganisms, such as mouthpiece in grocery store)
roller steel within fishing industry (rollers used in the fish industry in order to enhance the production of fish products).

Miscellaneous devices (c) comprise applications chosen from:
contact lenses (ordinary contact lenses)
intraocular lenses
cosmetic package products (packages for different cosmetic products)
water tanks (water tanks that contain tap water or recirculating water)
water pipes (pipes that transport tap water or recirculating water)
air conditioning, air and water cooling devices,
other devices for storage of products or materials where bacterial growth on surfaces of storage material is undesired.

In all these application, the antimicrobial agent of the invention is coupled to a surface of the device, as discussed above, in order to confer the antimicrobial effect.

In a preferred embodiment, the antimicrobial agent is coupled to a catheter surface, thereby providing a catheter being able to prevent growth and/or proliferation of microorganisms. Normally the inside and/or the outside surface of the catheter is coated with the agent of the invention. The coating process catheter surface may further be incorporated during or after the extrusion of the catheter, or as a separate step, prior to or after the assembly of the specific catheter. For treated catheter samples the microbial effect has been shown to remain after several years of storage under ambient conditions. Catheters that can be used in the invention are provided from commercial suppliers of catheter channels, e.g. Rehau, Habia, Vygon, Teknofluor, Optinova, Baxter etc.

In yet another aspect, the invention refers to a kit of parts for use in treating a surface with an antimicrobial agent, comprising, in separate compartments, (a) a precursor to the antimicrobial agent of claim 1, the precursor having the formula:

$$Z-L-S-S-(cysteine\ component)$$

wherein L, m, and cysteine component is as defined above, and Z is a ligand functionality as defined above that can react with a chemical compound Y as defined above to give the chemical compound X as defined above, and (b) necessary reagents in order to covalently bind the precursor to a surface, wherein the kit further comprises instructions for using the kit Necessary reagents may comprise any reagents that are necessary for performing a coupling reaction of Y and Z to obtain X (as outlined above), and would depend on the specific identity of Y and Z. The person skilled in the art would know what reagents that would be necessary in each situation.

Hereby, a kit is provided which can be used to treat any desired surface with the antimicrobial agent of the invention in order to give the surface antimicrobial properties.

The invention will now be further illustrated by way of examples. These examples are of illustrative purpose only, and shall not be regarded as limiting the scope of the invention in any way.

EXAMPLE SECTION

Methods

Analysis of Inhibition of Bacterial Growth on Modified Surfaces
Strains of Bacteria The following analysis was performed with three (3) different strains of bacteria, but the applications are not limited to these: A clinical isolate (from a patient with sepsis) of Gram positive bacterium *Staphylococcus aureus*, (a clinical isolate B5381), the Gram positive bacterium *Bacillus megaterium* (stain Bm11), the Gram negative bacterium *Escherichia coli* (strain D21). This selection of bacteria comprises both Gram positive and Gram negative bacteria including bacteria that are of significant problems clinically.

Preparation of Bacterial Culture to Determine Titer

The following description aims, but is not limited, to determine a titer of about 400 000-800 000 cfu/ml of different bacterial cultures, used as exposure source to evaluate inhibition of bacterial growth on functional surfaces. LB medium Tuna Bertani broth) has been inoculated with specific bacterial strain but not limited to this medium. The strain selected has been plated on an agar plate of selected medium the day before, and permitted to grow over night at 37° C. Several colonies were scraped from the plate and used to inoculate the medium which subsequently was allowed to grow up to an optical density of 0.4. The culture was diluted with the identical LB medium to an initial titer of approximately 400 000-800 000 cfu/ml. The number of bacteria was determined by plating serial dilutions and counting colonies in the appropriate dilutions. (Appropriate number of bacteria to count on a plate is between 30-300 as a general reference)

Pre-Treatment of Discs

The discs have been pre-sued in selected cases by incubation in:

a) Phosphate buffered saline (PBS)
b) Fetal Calf Serum (FCS)
c) Sterile LB medium,
during different time periods: 1 h, 1.5 h, 2.5 h, over night, 2 days or 7 days, as std in the examples below. Incubation has been made by rotation (200 rpm) at 37° C. in sterile eppendorf tubes.

Exposure of Functional Spices to Different Bacterial Strains

Surface-modified substrates, in the shape of circular discs, were placed in sterile eppendorf tubes. Each disc (5 or 9 mm in diameter) was placed in a specified volume (500 or 1000 μl, respectively) of the initial culture. These tubes are denoted "tube 1".

The discs in the initial cultures were incubated during 2.5 hrs at 37° C. by rotation (200 rpm).

An identical volume of the initial culture was incubated in parallel as a reference sample (denoted "postincubation culture"). This was used to determine to what levels the titer of the start culture (the culture that the discs were to be incubated in) would grow to, when not exposed to the discs. Control samples (same discs as used to compare the level of inhibition) were incubated with sterile LB medium, and subsequently handled in the same way, as a negative control to exclude contamination.

Assay for Analysis of Adherence of Viable Bacteria on Functional Surfaces

Subsequent to incubation (in the presently described case: 2.5 h), the disc was removed from each tube using a sterile pair of tweezers. The culture in which the disc had been incubated was in parallel transferred to a separate sterile eppendorf tube, and its titer was determined as described Tweezers and disc were dipped in a tube with about 4 ml sterile PBS solution, and the disc was then dropped in a second tube with PBS, denoted "tube 2". The disc was thereafter removed with a sterile pair of tweezers from tube 2. This procedure was performed in order to eliminate drops of surplus bacterial suspension resulting from the bacterial culture the disc had been incubated in, and hence to remove any bacteria that were not directly adherent to the disc surfaces. The washed disc was placed in an eppendorf tube—denoted "tube 3"—with 1 ml of PBS and was shaken roughly on a vortex rotator daring 10 minutes. Adherent viable bacterias—which have not been removed in the pious steps—is now detached from the surface into the PBS solution.

This solution is denoted "wash 1", and its titer was determined.

The disc is then removed with a sterile pair of tweezers via dipping in a tube with about 4 ml sterile PBS, and then dropped into another tube with about 2 ml sterile PBS, in the same way as described above. The disc is removed immediately with a sterilised pair of tweezers and transferred to a novel eppendorf tube, to which is added 1 ml sterile PBS, and the vortex procedure described is repeated. The PBS solution is transferred to a sterile eppendorf tube—denoted "wash 2"—and its titer was determined.

The disc was briefly placed on a sterile Kleenex wiper, to remove surplus drops of wash 2, and subsequently placed on a sterile agar plate of LB media, that was incubated over night at 37° C. The appearance of bacterial colonies, bacterial growth encircling the disc edges, was monitored.

Determination of Bacterial Titer in the Different Cultures and Wash Solutions

The dilutions were performed in LB media and selected dilutions (see below), where the colonies were analysed and counted.

A volume of 100 μl of serial dilutions of the following suspensions were spread:
1. Initial culture before dilution to incubation culture (OD ca 0.4):
2. The initial incubation culture (estimated to 400 000-800 000 cfu/ml); 1:100, 1:1000 and 1:10 000.
3. Post-incubation cultures (both reference and incubated with discs); 1:1000, 1:10000, 1:100000.
4. Negative control (medium without initial bacterial culture).
5. Wash 1:1:10 and 1:100.
6. Wash 2:1:1.

Example 1

Polycaprolactone (PCL; UC 787) in the shape of 1 mm thick flat samples with a diameter of 5 mm, were pre-irradiated with a pulse generator (6.5 MeV/75 Hz/4 μsec/60 mA) to a dose of 1 Mrad. The samples may then be grafted directly as described below or stored in liquid nitrogen prior to grafting.

Subsequent to the irradiation, alternatively after intermittent storage in liquid nitrogen, the PCL samples are introduced into a water solution of acrylic acid (20 w %) and 0.1 w % Mohr's salt, thermo-statted to 30° C. The solution was freed of oxygen by purging of inert gas which also acts as stirring. After 2 minutes in the acrylic acid solution, the samples were washed with large amounts of tap water of about 30° C. and are further on stored in deionized water prior to the succeeding surface modification. A number of samples, having a total area of 5 $cm^2$ and not grafted reference samples were deposited dung 6 hours with a specified amount of 0.0 M NaOH at ambient temperature. After potentiometric titration a surface concentration of $(1.8\pm0.2)\times10^{-5}$ mole $COOH/cm^2$ was determined.

Example 2

Separate solutions of 1-(3-dimethylaminopropyl)-3-etylkarbodiimid (EDC) and N-hydroxy-succinimide (NHS) (Sigma) in deionized water were mixed at 0° C., establishing a solution with concentrations of 0.3 M EDC and 0.075 M NHS respectively.

Acrylic acid grafted PCL samples, according to example 1, were washed in HEPES buffer (pH 7.4) and immersed into 20 ml of the EDC/NHS solution. After 10 minutes of agitation by shaking, the samples were rinsed in deionised water and were added with a solution of 0.04M 2-(2-pyridinylditio)-ethylamine-hydroklorid (PDEA) in a 0.1M borat buffer (pH 8.5). After 15 minutes of stirring the samples were rinsed in deionised water and added with a solution of 0.5M L-cysteine (Sigma) in 0.1M format buffer (pH 4.3) with 1M NaCl. After washing with 1M NaCl and deionized water, the samples were let to dry in air and kept in an excicator. Surface analysis with ESCA (XPS) measured a value of 6.8 atom % nitrogen.

Example 3

Samples of low density polyethylene (LDPE) were pre-irradiated with a dose of 2.5 Mrad, according to example 1. Subsequent to grafting with acrylic acid at 50° C. during 4 minutes, and all other identical conditions as in example 1, a value of carboxylation of $(2.7\pm0.2)\times10^{-5}$ mole $COOH/cm^2$, was detected Coupling reactions of PDEA and L-cystine to the acrylic acid grafted LDPE were performed the same way as for PCL in Example 2, and yielded a value of nitrogen of 6.0 atomic %, according to surface analysis with ESCA.

Example 4

Polyurethane catheters (Vygon®), having an outer diameter of 2 mm, were cut in lengths of 20 mm and pre-irradiated according to example 1, to a dose of 1 Mrad Grafting was performed according to example 2.

Example 5

Coupling onto an amine functional surface will be similar to the procedure in example 2. The difference is that the amine group within PDEA is replaced with a carboxylic group to obtain 2-(2-pyridyl dithio)ethyl carboxylic acid (PDEC). When reacting this compound with the amine groups on a surface the carboxylic group is activated separately with EDC/NHS prior to the reaction with the amine surface. The subsequent coupling with L-cysteine will then be made as in example 2.

Example 6

Reference surfaces were made according to examples 1 and 2 with the distinction that L-cysteine was coupled directly to the carboxylated PCL surface after activation with EDC/NHS via the amine group within the cysteine, i.e. the coupling step with PDEA was excluded, thus eliminating the disulphide bond obtained when coupling with PDEA, as in Example 2.

Example 7

Reference surfaces were made according to examples 1 to 3, differing in that acetylcysteine, instead of L-cysteine, were coupled according to the procedure describe in example 2.

Example 8

Reference surfaces were made according to examples 1 to 3, differing in that homocysteine, instead of L-cysteine, were coupled according to the procedure describe in example 2.

Example 9

Inhibition of bacterial growth in a culture of the Gram negative bacterium *Escherichia coli* (strain D21) was tested with PCL discs in 500 µl LB culture medium, for discs coupled with:
a) L-cysteine coupled to acrylic acid grafted PCL as in Example 1 and 2 (designated "Cys-discs")
b) Acrylic acid grafted PCL as in Example 1.

The initial titer of the culture was 513 000 cfu/ml and the postincubation titer of culture (reference, with no disc) was 28 000 000 cfu/ml.

Culture incubated with Cys-discs showed 125 times inhibition of growth in the culture medium during incubation compared to the postincubation culture (with no disc present). No inhibition was detected in the culture incubated with acrylic acid discs compared to posticubation culture (with no disc present).

Testing for adherent bacteria, Cys-discs showed a 100 folded inhibition of number of viable bacteria compared to discs with acrylic acid only, analysing the adherence of viable bacteria to discs.

Bacterial growth encircling the disc edges, placed on LB agar, was observed for discs with acrylic acid only and not for Cys-discs.

Example 10

Inhibition of baronial growth in the culture of *Staphylococcus aureus* (B5381, a clinical isolate) was tested with PE discs in 1000 µl bacterial culture.

Functional surfaces on discs were:
a) L-cysteine coupled to acrylic acid grafted discs according to Example 3 (prewashed/preincubated for 1.5 hr in PBS)
b) L-cysteine coupled to acrylic acid grafted discs according to Example 3 (prewashed/preincubated for 2 days in PBS)
c) L-cysteine coupled to acrylic acid grave discs according to Example 3 (prewashed/preincubated for 7 days in PBS)
d) Acrylic acid grafted discs according to Example 3

Initial titer of incubation culture was 400 000 cfu/ml and the postincubation titer was 10 000 000 cfu/ml.

Culture incubated with Cys-discs prewashed 1.5 hrs. exhibited 25 times inhibition of bacterial growth, Culture incubated with Cys-discs prewashed for 7 days displayed 17 times inhibition of bacterial growth.

Cys-discs prewashed for 2 days and 7 days showed approximately 50 times less viable bacteria than acrylic acid discs when tested for adherence of bacteria.

To summarise, the inhibition due to the cys-coupling is considered as permanent over at least 7 days.

Example 11

Inhibition of bacterial growth in a culture of the Gram positive bacterium *Staphylococcus aureus* (B5381, a clinical isolate) was tested with polyethylene (PE) discs in 1000 µl of LB media culture. Functional surfaces were:
a) L-cysteine coupled to acrylic acid grafted discs according to Example 3 (designated "Cys-discs")
b) Acrylic acid grafted discs according to Example 3 (designated acrylic discs)
c) Electron beam irradiated discs only, according to Example 3 (designed "EB discs")

In parallel, two control experiments with dissolved L-cysteine in culture were analysed. 50 µg/ml and 5 µg/ml.

The initial culture was set 10 fold higher (exceeding 4 million cfu/ml) than described in the assay procedure, which permit evaluation of the effect of adhesion of viable bacteria at an extreme exposure to bacteria.

Culture of Cys-discs demonstrated 8 times less growth compared to post incubation culture. EB discs exhibited no significant reduction compared to postincubation culture.

No inhibition was seen for the cultures with dissolved L-cysteine.

Cys-discs showed 25 to 40 times less viable adherent bacteria compared to acrylic acid discs and 21 to 27 times compared to EB discs in analysis for adherence of bacteria Bacterial growth encircling the disc edges was only seen for acrylic acid and EB discs.

The effect of Cys-coupling on adherence of viable *Staph aureus* bacteria onto the discs is still evident and significant despite that the system was quenched.

Example 12

Inhibition of bacterial growth in the culture of the *Escherichia coli* (strain D21) was examined with PE discs in 1000 µl of the bacterial LB media culture. Surfaces tested were:
a) L-cysteine coupled to acrylic acid grafted discs according to Example 3 (designated "Cys-discs")
b) N-acetyl-cysteine coupled to acrylic acid grafted discs according to Example 3 and 7 (designated "Acetyl-Cys-discs")
c) Acrylic acid grafted discs according to Example 3 denoted "Acrylic acid" discs All discs were preincubated in PBS over night.

The initial titer of the culture was 1 000 000 cfu/ml and the postincubation titer of culture (with no disc) was 50 000 000 cfu/ml.

Cys-discs displayed 45 times inhibition of growth in the cue medium compared to the post-incubation culture (with no disc present) during the incubation. Acetyl-Cys-discs showed 10 times inhibition in the culture medium. No inhibition was detected in the culture with acrylic acid disc present.

Cys-discs showed 70 times less viable bacteria than acrylic acid discs while acetyl cysteine discs showed 7 times less viable bacteria than acrylic acid discs when investigated for bacterial adherence.

Bacterial growth encircling the disc edges was detected around all acrylic acid discs, partially around the Acetyl-Cys-discs, while no bacteria were observed around the Cys-discs Example 13

Inhibition of bacterial growth in a culture of *Escherichia coli* (strain D21) was tested with PE discs in 1000 µl bacterial culture, for disc coupled with
a) L-cysteine coupled to acrylic acid grafted discs according to Example 3 (designated "Cys-discs")
b) L-cysteine coupled via amino group to acrylic acid grafted PE discs according to Example 3 and 6 (denoted "Amino coupled Cys-discs")
c) Acrylic acid grafted discs according to Example 3 (designated "acrylic acid discs")

All discs were preincubated in sterile LB medium over night. The initial titer of the culture was 680 000 cfu/ml and the postincubation titer of culture (with no disc) was 32 000 000 cfu/ml.

Cys-discs exhibited 26 times inhibition of bacterial growth in the culture medium compared to the postincubation culture (with no disc present) during incubation. Neither the amino coupled Cys-discs nor the acrylic acid disc showed inhibition in the culture medium.

Cys-discs showed 100 to 140 times less viable adherent bacteria than acrylic acid discs while amino coupled Cys-discs exhibited no reduction in number of viable adherent bacteria compared to acrylic acid discs, as tested for adherence of bacteria.

Significant bacterial growth encircling the disc edges, analysed on LB agar plates after the washing procedures, was detected for all amino coupled discs and acrylic acid discs, but not for Cys-discs.

Example 14

Inhibition of bacterial growth in a culture of *Staphylococcus aureus* (B 5381, a clinical isolate) was tested with PE discs in 1000 µl LB medium bacterial culture with extreme bacterial concentrations
Functional surfaces on discs were:
a) L-cysteine coupled to acrylic acid grafted discs according to Example 3 (designated "Cys-discs")
b) Homocysteine coupled to acrylic acid grafted discs according to Example 3 (denoted "Homocysteine discs")
c) Acrylic acid grafted discs according to Example 3 (designated "acrylic acid discs")

The initial titer of the culture was 4 000 000 cfu/ml and the postincubation titer of culture (with no disc) was 80 000 000 cfu/ml.

Cys-discs showed 13 times inhibition of growth in the culture medium compared to the postincubation culture with no disc present. Homocysteine discs showed 20 times inhibition in the culture medium.

Cys-discs showed approximately 4 to 10 times less viable adherent bacteria compared 28 to acrylic acid discs and the homocysteine discs displayed 2 to 4 times less viable bacteria compared to acrylic acid discs, when tested for adherence of viable bacteria under extreme exposure conditions. A detectable effect was obtained despite the quenched conditions for both cysteine and homocysteine discs.

Example 15

The long-term duration and stability of the antibacterial effect was tested by using surface modified catheters stored for over 3 years.

Inhibition of bacterial growth in the culture of *Escherichia coli* D21 was tested with Polyurethane catheters Vygon (Example 4) in 1000 µl LB medium bacterial culture. These cysteine modified catheter samples had been stored for 3 years under ambient conditions together with reference surfaces EB irradiated and acrylic acid grafted according to example 4). Prior to the experiment, these catheters (20 mm long) were cut in half, generating two 10 mm long pieces. Functional surfaces on discs were:
d) L-cysteine coupled coupled to acrylic acid grafted Vygon catheters according to Example 4, denoted Cys-catheters (prewashed/preincubated for 2 hr in PBS)
e) EB irradiated Vygon Catheters (part of example 1 and example 4) (prewashed/preincubated for 2 hr in PBS)

Initial titer of incubation culture was 264 000 cfu/ml and the postincubation titer was 52 000 000 cfu/ml, when no catheter sample was present.

Culture incubated with Cys-catheters (prewashed 2 hrs) exhibited 34 times inhibition of bacterial growth compared with post-culture with no disc.

Culture incubated with EB irradiated Vygon Catheters (prewashed 2 hrs) (control materials) exhibited no inhibition compared to postincubation culture with no catheter. Cys-catheters showed 130 times less viable bacteria compared to EB irradiated Vygon catheters when tested for adherence of bacteria.

To summarize, storage of the product for prolonged times does not critically affect the antibacterial properties of the surface modification.

Example 16

Inhibition of bacterial growth in a culture of *Staphylococcus aureus* (B 5381, a clinical isolate) was tested with polyurethane catheter surface, in 800 ul of LB medium bacterial culture. Discs were prewashed for 1-5 hours in PBS. These catheters were cut into pieces of 5×4 mm. and pre-irradiated according to example 1, to a dose of 1 Mrad. Grafting was performed according to example 2.

Functional guru on discs were:
a) PDEA-coupled acrylic acid grafted samples were made essentially following the procedure described in Example 1 and 2 with the following modifications: 5 min grafting times and ultrasonic bath washing 15 minutes subsequent to grafting.
b) The PDEA samples obtained in (a) were used for coupling L-cysteine following the procedure described in Example 2.

The antibacterial effect was compared for the samples of (a) and (b) to investigate apossible significant influence of the PDEA component prior to the cysteine coupling The initial titer of the culture was 800 000 cfu/ml and the postincubation titer of culture (with no disc) was 19 000 000 cfu/ml. No difference in postincubation titer was observed between the sample types (a) and (b). Cys-acrylic acid samples (b) showed approximately 35 times less viable adherent bacteria compared to PDEA-coupled acrylic acid samples (a) when tested for adherence of viable bacteria. This experiment verifies that the cys-component is essential for the antibacterial effect.

Example 17

Inhibition of bacterial growth in a culture of *Staphylococcus aureus* (B5381) was tested with polyurethane (PUR) discs in 500 µl of LB medium bacterial culture. These samples were cut in square discs of 5×5 mm.

Functional surfaces on discs were:
(a) PUR samples were EB radiated to 1 Mad and grafted for 3 minutes at 35° C. with acrylic acid and extensively washed in warm tap water and MilliQ water including an ultrasonic washing bath for 15 minutes, followed by coupling with PDEA and finally L-Cysteine according to the procedures described in example 1 and 2. These samples were denoted "PDEACys"
(b) A surface was made as follows: PDEA with eqimolar amount triethylamine was reacted with an equimolar amount of acryloyloloride in a dry solvent. The product 2-(2-pyridinyldito)-ethylacrylamide, herein denoted "PDEAm" was purified by precipitation in diethyleter which was repeated until a colourless clear filtrate was obtained. The slightly yellow product was dried under vacuum. A solution containing 2.2 mmol (0.5 g) PDEAm and 16.1 mmol (1 g) acrylic acid in 5 ml MilliQ water was deareated by purging with Argon for 10 minutes and thermostatted to 35° C. The EB irradiated PUR samples (a) were taken from the liquid nitrogen storage and immersed in the solution where the Argon stream also acted as sting device. The grafting reaction was interrupted after 8 minutes and the samples were washed thoroughly in warm tap water and MilliQ water including an ultrasonic washing bath for 15 minutes. L-Cysteine was coupled according to the procedures described in example 1 and 2. The samples were dried under vacuum. These samples are denoted "TDRAm-Cys".

A comparison was made between PDEA-Cys (a) and PDEAm-Cys (b). The initial titer of the culture was 500 000 cfu/ml and the postincubation titer of culture (with no disc) was 20 000 000 cfu/ml.

PDEA-Cys (a) showed 45 times inhibition of postincubation titer compared to culture with no disc present.

PDEAm-Cys (b) showed 50 times inhibition of postincubation titer compared to culture with no disc present.

PDEA-Cys (a) and PDEAm-Cys (b) show equal inhibition of viable bacteria colony forming units when tested for adherence of viable bacteria using the method described above. No bacterial growth encircling the disc edges, as analysed on LB agar plates after the washing procedures, was detected for any of the samples.

Example 18

Inhibition of bacterial growth in a culture of the Gram positive bacterium *Bacillus megaterium* (strain Bm 11), was analysed with a PCL disc in 500 µl bacterial culture in LB medium. Functional surfaces were:
a) L-cysteine coupled to acrylic acid grafted PCL as in Example 1 and 2 (designated "Cys-discs")
b) Acrylic acid grafted PCL as in Example 1

The initial titer of the culture was 292 000 cfu/ml and the postincubation titer of culture (with no disc) was 9 850 000 cfu/ml.

For tubes with Cys-discs there was 13.5 times inhibition of bacterial growth in the culture incubated with the disc during incubation compared to the reference postincubation culture (with no disc present). Discs with only acrylic acid displayed no inhibition of bacterial growth in the culture compared to the control with no disc present.

Testing for adherence of viable bacteria showed 10 to 13 times less viable bacteria on Cys-discs compared to acrylic acid discs.

Bacterial growth encircling the disc edges was only found for discs coupled with acrylic acid when the discs were set on LB plates after the washing procedure and incubated overnight.

Example 19

Cytotoxicity was tested by incubation of the different functional discs in Peripheral blood mononuclear cells (PBMC) from healthy blood donors.

The samples tested were:
a) Cys-discs. (Example 2)
b) Acrylic acid discs. (Example 1)
c) Electron Beam irradiated discs. (part of Example 1) (denoted "EB discs")
d) Control cells incubated without any disc present).

The determinations were made after 24, 48 and 69 hrs, respectively. The amount of dead cells were 4% to 7% after 18 hours of incubation in PBMC for all disc types and controls, indicating no significant differences between Cys-discs, acrylic acid discs, EB discs or control cells incubated without any disc present. This was seen irrespective of whether discs had been prewashed in PBS or not. The parts of dead cells were 10% to 15% in unwashed Cys-discs and acrylic acid discs after 48 hours of incubation. There was no notable difference in the number of dead cells between washed Cys-discs, acrylic acid discs, EB discs, compared to control cells without any disc present (5-6%).

The proliferation of T-cells was studied by stimulation with mitogen phytohemaglutinin (PHA). PBMC from healthy blood donors were isolated and cells were stimulated with PHA (Sigma, St Louise, Mo., USA), in triplicates. The cultures were pulsed with 1 µCi methyl-3H-thymedine (Amersham, LIFE SCIENCE) at 2 days post stimulation. Cells were harvested onto filters, utilising a plate harvester (Harvester 996, Tomtec, Hamden, Conn., USA) the subsequent day, according to the manufacturer's instructions, and counted in an automated counter (1450 MicroBeta Trilux, WALLAC, Sweden AB). The results were expressed as counts per minute (cpm). No difference in the T cell proliferation was seen between any disc type and controls.

The following test was performed in order to investigate if the ability of monocytes derived from PBMC to differentiate into macrophages was negatively affected by the exposure to the different types of discs.

PBMC:s from healthy blood donors plated onto petri dishes (Primaria, Falcon, Becton Dickinson) at a cell concentration of 10-18×10$^6$ cells/ml in Iscove's Modified medium with 2 mM L-glut nine, 100 U/ml penicillin, 100 µg/ml streptomycin (Gibco BRL, Grand Island, N.Y.), 10% AB serum and incubated at 37° C. over night. The non-adherent cells were removed the following day. The cultures were extensively washed and the monocyte enriched cells were stimulated by addition of a 24 hours allo-supernatant. The allosupernatant was prepared as follows: PBMC:s from different blood donors were mixed and incubated for 24 hours in Iscove's complete medium. Thereafter, the supernatant was collected, cleared by centrifugation and used to stimulate single monocyte cultures. At 2 to 3 days of post stimulation, the cultures were washed with Iscove's medium and thereafter cultured in 60% AIM-V medium, 30% Iscove's modified medium and 10% AB serum, with the addition of L-glutamine, penicillin and streptomycin (complete 60/30 medium). The medium was changed to fresh complete 60/30 medium every 3-4 days.

No significant difference was seen between control cells or cells exposed to the different type of discs, i.e. nice or healthy macrophage cultures were seen in all the Petri dishes.

Example 20

Cytotoxicity was also analysed by measuring the haemolytic effect of the different disc types by placing the discs on blood agar, either just on top or by pushing the discs into the blood agar.

The samples tested were:
a) unwashed Cys-discs. (Example 3)
b) Cys-discs pretreated with LB media. (Example 3)
c) Cys-discs pretreated with fetal calf serum (FCS). (Example 3)
d) Cys-catheters Vygon. Example 4)

The diameter of lysed zones was measured after incubation at 37° C. over night. A positive control was located in the centre of each blood agar plate. At inspection, the discs were removed and the area under, and around the location of the discs, were analysed.

No lysis could be detected for none of the disc types analyses

A yellow colour was detected of about 4 to 5 mm from the edge of the discs for unwashed Cys discs. For pretreated discs, with either LB media or fetal calf serum (FCS), a very weak change of colour at the nearest edge of the disc was noted.

In conclusion, the Cys-discs have no significant cytotoxic effect on human blood cells.

The invention claimed is:

1. Antimicrobial agent comprising a substrate, wherein said substrate is a solid surface or a polymer bound to said solid surface by covalent binding or adsorption, with a covalently bound cysteine component, wherein said cysteine component is bound through an S—S bridge via a spacer molecule to the substrate, the spacer comprises a carbon chain, optionally interrupted by one or more heteroatoms, the chain is optionally substituted with one or more alkyl groups, wherein said cysteine component is cysteine, a cysteine analogue or a cysteine derivative, wherein said substrate is a part of a device, an apparatus and/or a surface selected from (a) a medical device or (b) a grocery device, wherein the S—S bridge comprises one S from the thiol group of the cysteine component and one S from the spacer.

2. Antimicrobial agent according to claim 1 having the formula substrate-X-L-S-cysteine component, wherein
L is a spacer molecule selected from the group comprising $(CH_2)_m$ where m is 1-20 optionally interrupted by one or more heteroatoms, optionally substituted by one or more alkyl groups; and $(CH_2CH_2O)_n(CH_2)_p$ where n is 1-1000 and p is 1-20, wherein the $(CH_2)_p$ segment is bound to the disulphide bond bridge and may optionally also be positioned between $(CH_2CH_2O)_n$ segments;
X is linking group from the coupling reaction between the substrate and L.

3. Antimicrobial agent according to claim 1 having the formula $$R_1\text{—}X\text{-}L\text{-}S\text{-(cysteine component)} \quad (1)$$

wherein
$R_1$ is the substrate
X is a linking group obtained by a chemical coupling reaction
L is $(CH_2)_m$ or $(CH_2CH_2O)_n(CH_2)_p$
m is 1-8, n is 1-100 and p is 1-10
where the $(CH_2)_p$ segment when occurring together with the $(CH_2CH_2O)_n$ is positioned between the $(CH_2CH_2O)_n$ segment and the disulphide bond.

4. Antimicrobial agent of claim 2, wherein -L-S-(cysteine component) comprises the compound of formula (2) or (3):

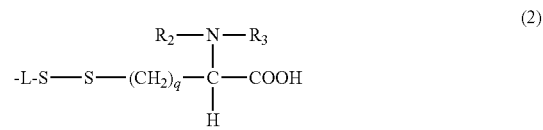

wherein $R_2$, $R_3$ is hydrogen or alkyl with 1 to 25 carbon atoms in any combination; q is from 1-20 or

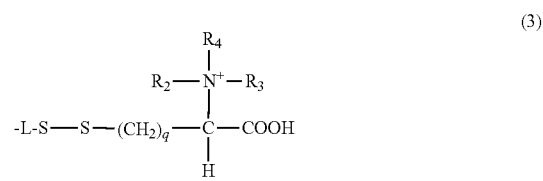

wherein $R_2$, $R_3$, $R_4$ are alkyl substituents with 1-25 carbon atoms in any combination; q has a value in the interval 1-20.

5. Antimicrobial agent according to claim 4 where one of $R_2$ or $R_3$ as described in formula (2) is attached via an amide bond comprising nitrogen of the cysteine component.

6. A method for preventing or inhibiting growth and/or proliferation of Gram-positive and/or Gram-negative bacteria comprising contacting microorganisms with the antimicrobial agent of claim 1.

7. The method of claim 6, wherein the Gram-negative bacteria comprises *Escherichia coli* or the Gram-positive bacteria comprises *Staphylococcus aureus* or *Bacillus megaterium*.

8. The antimicrobial agent according to claim 1, wherein the device, apparatus or surface is chosen from artificial skin for burning wounds, a dialysis device, an ear drainage device, ear implants, a hearing aid device, heart and lung machine tubings, hydrocephalus drainage, a syringe, stomis, wound care devices, suture materials, catheters, dental products, tubing or equipment used for parenteral administration of liquids, solutions, infusions, drug delivery, implants in the body, insulin pump, nerve guidelines, pacemakers, drainage from within the body or intraluminal stents.

9. Method for manufacturing an antimicrobial device comprising a substrate, wherein said substrate is a solid surface or a polymer bound to said solid surface by covalent binding or adsorption, with a covalently bound cysteine component, wherein said cysteine component is bound through an S—S bridge via a spacer molecule to the substrate, the spacer comprises a carbon chain, optionally interrupted by one or more heteroatoms, the chain is optionally substituted with one or more alkyl groups, wherein said cysteine component is cysteine, a cysteine analogue or a cysteine derivative, wherein the S—S bridge comprises one S from the thiol group of the cysteine component and one S from the spacer the method comprising the step(s) of:

covalently binding a ligand -L-S-(cysteine component) to functional groups at the surface of the device, or to a polymer which is subsequently immobilized on the surface of the device.

10. Antimicrobial agent comprising a substrate, wherein said substrate is a solid surface or a polymer bound to said solid surface by covalent binding or adsorption, with a covalently bound cysteine component, wherein said cysteine component is bound through an S—S bridge via a spacer molecule to the substrate, the spacer comprises a carbon chain, optionally interrupted by one or more heteroatoms, the chain is optionally substituted with one or more alkyl groups, wherein said cysteine component is cysteine, a cysteine analogue or a cysteine derivative wherein the S—S bridge comprises one S from the thiol group of the cysteine component and one S from the spacer said agent having the formula: (PUR-polyacrylic acid)-CONH—CH$_2$—CH$_2$—S—S—CH$_2$—CH(NH$_2$)—COOH.

11. A device comprising a substrate, wherein said substrate is a solid surface or a polymer bound to said solid surface by covalent binding or adsorption, with a covalently bound cysteine component, wherein said cysteine component is bound through an S—S bridge via a spacer molecule to the substrate, the spacer comprises a carbon chain, optionally interrupted by one or more heteroatoms, the chain is optionally substituted with one or more alkyl groups, wherein said cysteine component is cysteine, a cysteine analogue or a cysteine derivative, and wherein said device is chosen from (a) medical devices and (b) grocery devices, wherein the S—S bridge comprises one S from the thiol group of the cysteine component and one S from the spacer.

12. The device according to claim 11, said substrate having the formula substrate-X-L-S-(cysteine component), wherein L is a spacer molecule selected from the group comprising (CH$_2$)$_m$ where m is 1-20, optionally interrupted by one or more heteroatoms, optionally substituted by one or more alkyl groups; and (CH$_2$CH$_2$O)$_n$(CH$_2$)$_p$ where n is 1-1000 and p is 1-20, wherein the (CH$_2$)$_p$ segment is bound to the disulphide bond and may optionally also be positioned between (CH$_2$CH$_2$O)$_n$ segments;

X is linking group from the coupling reaction between the substrate and L.

13. The device according to claim 11, said substrate having the formula (R$_1$—X-L-S-(cysteine component))     (1)

wherein

R$_1$ is the substrate

X is a linking group obtained by a chemical coupling reaction

L is (CH$_2$)$_m$ or (CH$_2$CH$_2$O)$_n$(CH$_2$)$_p$ m is 1-8, n is 1-100 and p is 1-10 where the (CH$_2$)$_p$ segment when occurring together with the (CH$_2$CH$_2$O)$_n$ is positioned between the (CH$_2$CH$_2$O)$_n$ segment and the disulphide bond.

14. The device claim 13, wherein -L-S-(cysteine component) comprises the compound of formula (2) or (3):

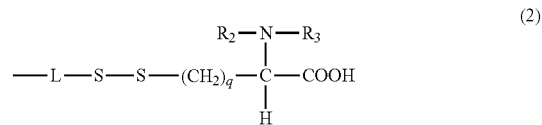

wherein R$_2$, R$_3$ is hydrogen or alkyl with 1 to 25 carbon atoms in any combination; q is from 1-20 or

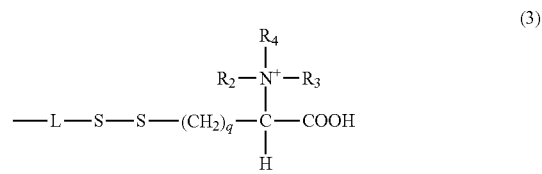

wherein R$_2$, R$_3$, R$_4$ are alkyl substituents with 1-25 carbon atoms in any combination; q has a value in the interval 1-20.

15. The device according to claim 14 where one of R$_2$ or R$_3$ as described in formula (2) is attached via an amide bond comprising nitrogen of the cysteine component.

16. The device according to claim 11, wherein the device is chosen from artificial skin for burning wounds, a dialysis device, an ear drainage device, ear implants, a hearing aid device, heart and lung machine tubings, hydrocephalus drainage, a syringe, stomis, wound care devices, suture materials, catheters, dental products, tubing or equipment used for parenteral administration of liquids, solutions, infusions, drug delivery, implants in the body, insulin pump, nerve guidelines, pacemakers, drainage from within the body, or intraluminal stents.

17. Method for manufacturing an antimicrobial device according to claim 11 comprising covalently binding a ligand -L-S-(cysteine component) to functional groups at the surface of the device, or to a polymer which is subsequently immobilized on the surface of the device wherein L comprises a carbon chain, optionally interrupted by one or more heteroatoms, the chain is optionally substituted with one or more alkyl groups, and wherein said cysteine component is cysteine, a cysteine analogue or a cysteine derivative.

* * * * *

UNITED STATES PATENT AND TRADEMARK OFFICE
CERTIFICATE OF CORRECTION

| | | |
|---|---|---|
| PATENT NO. | : 8,563,612 B2 | Page 1 of 1 |
| APPLICATION NO. | : 11/886759 | |
| DATED | : October 22, 2013 | |
| INVENTOR(S) | : Wirsen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 276 days.

Signed and Sealed this
Ninth Day of June, 2015

Michelle K. Lee
*Director of the United States Patent and Trademark Office*